United States Patent
Laney

(10) Patent No.: US 11,027,035 B1
(45) Date of Patent: Jun. 8, 2021

(54) SYSTEM, METHOD FOR PROVIDING AROMATHERAPY

(71) Applicant: Rayford Laney, Laguna Beach, CA (US)

(72) Inventor: Rayford Laney, Laguna Beach, CA (US)

(*) Notice: Subject to any disclaimer, the term of this patent is extended or adjusted under 35 U.S.C. 154(b) by 0 days.

(21) Appl. No.: 16/694,704

(22) Filed: Nov. 25, 2019

Related U.S. Application Data

(60) Provisional application No. 62/882,138, filed on Aug. 2, 2019.

(51) Int. Cl.
| | |
|---|---|
| *A61L 9/02* | (2006.01) |
| *A61K 36/32* | (2006.01) |
| *A01N 65/08* | (2009.01) |
| *A61K 9/00* | (2006.01) |
| *A61K 36/537* | (2006.01) |
| *A61K 36/53* | (2006.01) |
| *A01N 65/22* | (2009.01) |

(52) U.S. Cl.
CPC ............. *A61L 9/02* (2013.01); *A01N 65/08* (2013.01); *A01N 65/22* (2013.01); *A61K 9/007* (2013.01); *A61K 36/32* (2013.01); *A61K 36/53* (2013.01); *A61K 36/537* (2013.01)

(58) Field of Classification Search
CPC ........... A61L 9/02; A61K 9/007; A61K 36/32; A61K 36/537; A61K 36/53; A01N 65/22; A01N 65/08
See application file for complete search history.

(56) References Cited

PUBLICATIONS

Scents-of-earth.com, How to make your own incense—we have what you need. (Year: 2018).*
WHO Expert Committee on Drug Dependence Critical Review, Cannabis and Cannabis Resin, WHO . . . (Year: 2018).*
Desert Extracts, Slow Burn Concentrates. (Year: 2019).*
https://www.webmd.com/balance/news/20190521/are-there-health-benefits-from-burning-sage (Year: 2019).*

* cited by examiner

*Primary Examiner* — Carlos A Azpuru
(74) *Attorney, Agent, or Firm* — Rutan & Tucker, LLP; Kyle M. St. James

(57) ABSTRACT

A pressed biomass component is disclosed. The pressed biomass component includes plant or animal material that is compressed by a press plate apparatus by application of pressure within a range of 1000 to 36000 pounds per square inch (PSI). The pressed biomass component is a resultant of the application of the pressure to the plant or animal material and typically has a weight of 0.5-10 grams. The pressed biomass component of claim 1 may be formed in a disc shape including a curved perimeter, a top surface and a bottom surface oriented in parallel with the top surface; thus, resembling a coin. The application of pressure to the press plate apparatus forms the pressed biomass component to support a desired burn time when placed on a heating apparatus. The heating apparatus often includes a ceramic bulb having a wattage within a wattage range of 50 w-150 w.

24 Claims, 7 Drawing Sheets

SYSTEM, METHOD FOR PROVIDING AROMATHERAPY

CROSS-REFERENCE TO RELATED APPLICATIONS

This application claims the benefit of priority to U.S. Provisional Application No. 62/882,138, filed Aug. 2, 2019, the entire contents of which are incorporated by reference herein.

FIELD

Embodiments of the disclosure relate to the field of aromatherapy. More specifically, embodiments of the disclosure relate to a pressed biomass component that may be formed using various materials, have various sizes and take various shapes. Additional embodiments of the disclosure relate to an apparatus configured to apply heat to the pressed biomass component.

GENERAL BACKGROUND

The background description includes information that may be useful in understanding the present invention. It is not an admission that any of the information provided in this application is prior art or relevant to the presently claimed invention, or that any publication specifically or implicitly referenced is prior art.

Scientific evidence has shown that the role of fragrances and benefits of the field aromatherapy can be used to modulate human emotions. As such, consumer demand of aromatherapy and air purification products has increased in the recent past. In one particular example, various market studies have shown that sage in its natural form (e.g., unprocessed, loose leaf) has been in high demand. However, in the past few years as aromatherapy and air purification practices have increased, there has been no change to how the consumer consumes loose leaf sage and various other plant components as found in their natural form.

For example, currently on the market there are a plurality of different aromatherapy and/or air purifying products including wax burners, incense sticks or cones, essential oil burners, oil diffusers and candles. For example, a wax burner or warmer includes at least a module for receiving a wax component and a heater module. Incense is often found in a solid form, e.g., bark powder or birch bark powder formed into wood substrates, to which flavoring is applied by combining a mixture of ingredients and drying the mixture. Essential oil burners often include a heating surface and a light source with a fragrance disk on which an essential oil is placed. The heating surface and/or the light source heats the essential oil causing the emission of a fragrance. An essential oil diffuser may include a reservoir, such as glass, for holding an essential oil (or other liquid fragrance) and a plurality of sticks that facilitate the evaporation of the essential oil (e.g., the essential oil travels through the sticks and evaporates). Further, candles may be formed from a plurality of materials such as paraffin wax, beeswax, a mixture of polymer and mineral oil, or plant waxes such as palm wax or soybean wax.

However, it should be noted that each of the aromatherapy and/or air purifying products discussed above have several disadvantages. For example, wax burners and candles leave a byproduct of melted wax that is extremely hot when in use and shortly thereafter, and leaves a residue that is inconvenient to clean. Candles and some incense sticks are to be lit and must remove lit in order to diffuse the intended fragrance. Essential oil diffusers are easy to knock over causing spillage of the essential oil. Further, some products such as candles and incense have a short life span and cannot be refilled.

Further, the products discussed above are often comprised of processed versions of the various ingredients. For example, wax burners often include a sage fragrance as an option; however, the sage is not in an unaltered, natural form. Similarly, incense sticks may include a processed version of sage. Further, some products such as essential oil burners and diffusers, are unable to supply a strong fragrance with some materials, such as sage.

With respect to some materials referenced above, these have been used for hundreds of years for medicinal or holistic purposes in various locations includes residential locations, medical environments, yoga/exercise studios, and chiropractor offices. Additionally, some use burning these materials for holistic purposes. For example, some burn sage as a method of purifying or removing certain particles within the air. Burning has also been shown to release negatively charged particles into the air, which destroy certain bacteria.

However, burning of sage (and other materials) has several disadvantages referred to above. As a specific example with respect to sage, the current practice is to burn loose leaf sage 100 of FIG. 1. In particular, the loose leaf sage is often burned after being rolled in a smudge stick 200 of FIG. 2. One disadvantage, other than the inherent dangers of lighting a material on fire with an open flame, is that the smudge stick 200 needs to be constantly attended to, as well as maintained, by fanning the lit portion of sage with oxygen in order to maintain the flame.

SUMMARY OF THE INVENTION

The present invention provides improved apparatuses, systems, and methods for releasing fragrance and flavonoids into the surrounding air. Exemplary embodiments of the disclosure are directed to the manufacture of a component that is easily heated in a safe and efficient manner and releases a fragrance and/or flavonoids into the proximate airspace. For example, a mechanical press compresses a biomass and, optionally, other materials into a compact component. In some embodiments, no binding element is utilized due to the pressure applied by the mechanical press and the substance(s) being pressed.

Further embodiments of the disclosure are directed at providing an aromatherapy and/or air purifying product lacking the disadvantages of current products discussed above. In particular, some embodiments apply constant heat directly or indirectly to the pressed biomass component (referred to herein as a "coin"). Thus, the coin may be lit by supplying a controlled, constant heat surface thereby emitting a fragrance, as well as the air purifying substances (e.g., ions) with respect to applicable materials (e.g., sage). Additionally, various studies have shown that burning or smoldering sage, e.g., white sage (*Salvia apiana*), releases negative ions into the surrounding environment through the smoke produced, which has antiseptic, bacteria killing-properties.

Such aromatherapy and/or air purifying products disclosed herein provide for a hands-free, maintenance-free burning or smoldering of one or more coins, without the worry of loss of ignition or the potential for fire hazards. Further, the heating apparatus disclosed herein used to heat the coins does not utilize an open flame but instead includes an enclosed heating element, such as a light bulb. Additionally, the heating apparatus may include a cover that surrounds the heating element and the coin during the heating process. The combination of the heating element and the cover provide numerous safety benefits over current aromatherapy and/or air purifying products on the market due to the reduced risk of starting fires.

BRIEF DESCRIPTION OF THE DRAWINGS

The present disclosure is illustrated by way of example, and not limitation, in the figures of the accompanying drawings, in which like reference numerals indicate similar elements and in which.

DETAILED DESCRIPTION

Figure 1:
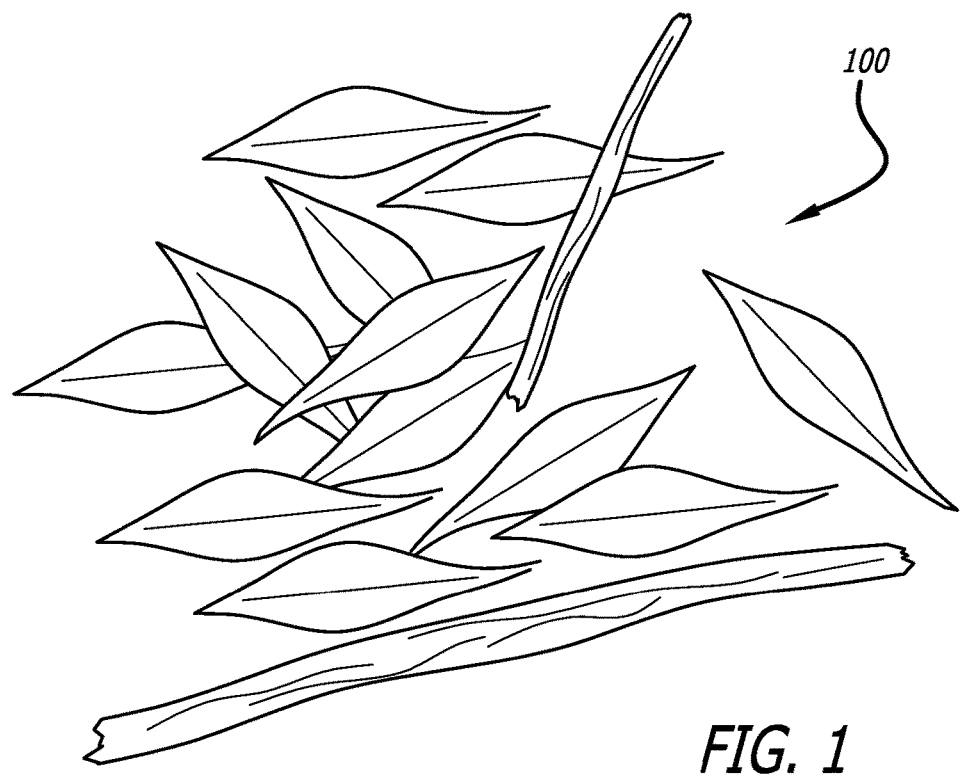
FIG. 1 is an illustration of a biomass in accordance with some embodiments.
Figure 2:
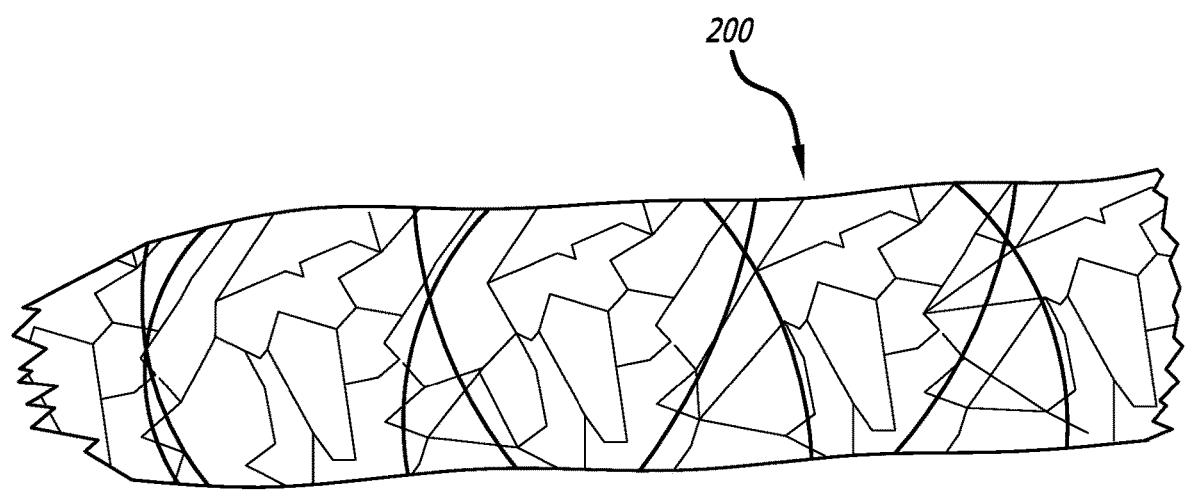
FIG. 2 is an illustration of a smudge stick in accordance with some embodiments.

Various embodiments of the disclosure provide methods, systems and apparatuses for providing aromatherapy. More specifically, embodiments of the disclosure relate to a heating apparatus configured to heat a coin, wherein the coin is manufactured from unprocessed, raw plant stock through the application of pressure, such as from a hydraulic piston.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive. Further, as used in the disclosure, the meaning of "in" includes "in" and "on" unless the context clearly dictates otherwise.

I. Coin

As referenced above, some embodiments of the disclosure are directed to a pressed biomass component, referred to herein as a "coin." A coin, or pressed coin, may be formed using various materials, have various sizes and take various shapes. Some shapes contemplated include, but are not limited or restricted to, circles, spheres, triangles, pyramids, squares, ovals, hearts, rectangles, diamonds, pentagons, hexagons, octagons, tetragons, decagons, rhombuses, crescents, cylinders, trapezoids, etc. The coins are three-dimension (3D) objects that vary in height, length, width and weight depending on the material or materials used, the pressure applied to the biomass during the pressing stage, the amount of biomass used and specific use-cases (e.g., desired burning time). In some embodiments, a pressed coin may have a weight within the range of 0.5-10 grams.

The pressed coins may be comprised of plant stock listed by themselves, or in combination with other materials such as (i) plants, (ii) spices, (iii) essential oils, and/or (iv) other flavonoids. Such materials may include, but are not limited or restricted to, herbs, flowers, woods, lavender, peppermint, lemon, clover, eucalyptus, frankincense resin, tea tree, chamomile, rosemary, jasmine, cedar wood, myrrh, lemongrass, pine, sage, desert sage, clove, cinnamon, dandelion, chamomile, ginger, basil, white sage, rosemary, thyme, lilac, rose, amaranth, Ylang-ylang, mugwort, aspen, blue spruce, sweet grass, Palo Santo, apiaceae, solanaceae, fabaceae, steraceae and juniper. The material used may be in any form such as loose leaves, powder, shavings, petals, essential oil, etc.

In some instances, coins will also be pressed with perfumes and various aromas (e.g., perfumes may be applied to the biomass prior to or following the application of pressure). The terms "perfumes" and various aromas" may refer to any form of the ingredients discussed above including, but not limited to, liquids and/or solids including powders, raw products (leaves, steams, fruit, bark, etc.), crushed, shredded, etc.

Further, some coins may include a binding element, e.g., makko powder. The binding element is mixed with the biomass prior to pressing, and during the pressing stage, the binding element is compressed with the biomass resulting in a coin that will not separate when removed from the coin pressing apparatus, as discussed below. In other embodiments, a binding element is not used, as some materials remain sufficiently bound without inclusion of a binding element.

Figure 3A:
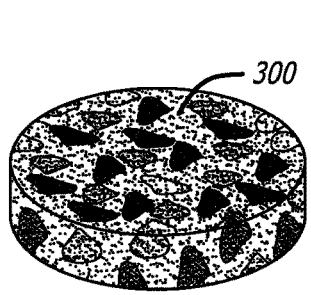
FIG. 3A is an illustration of a side perspective of a first coin in accordance with some embodiments.

Referring to FIG. 3A, a side perspective of a first coin is illustrated in accordance with some embodiments. The coin 300 is a mixture of lavender, sage and makko powder, pressed together at a pressure range of 1000 to 36000 PSI (pounds per square inch). Specifically, the coin 300 may be formed by application of pressure within a range of 1800 to 4000 PSI. Further, in one specific embodiment, the coin 300 may be formed by application of pressure at approximately 3800 PSI. In a first embodiment, the coin 300 may comprise 100% sage, such as white sage. In a second embodiment, the percentages by weight compared to total weight of the coin 300 per formulation are: (1) sage (loose leaf) by weight percent of 74.8%, (2) lavender (loose leaf) by weight percent of 24.9%, and (3) makko powder by weight percent 0.25%. In yet another embodiment, the coin 300 may comprise 100% Palo Santo and be pressed with the application of approximately 18000 PSI. In another embodiment, the percentages by weight compared to total weight of the coin 300 per formulation are: (1) sage by weight percent within a first range of 70-77%, (2) lavender by weight percent within a second range of 20-27%, and (3) makko powder by weight percent of within a third range of 0.1-2%.

Figure 3B:
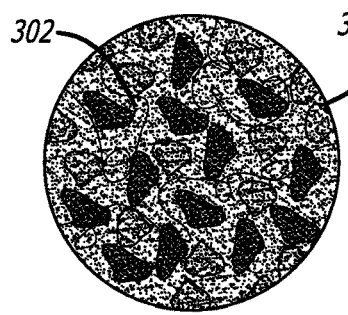
FIG. 3B is an illustration of a top perspective of the first coin of FIG. 3A in accordance with some embodiments.
Figure 3C:
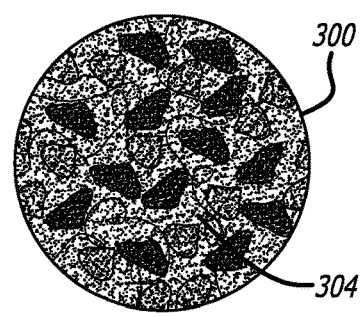
FIG. 3C is an illustration of a bottom perspective of the first coin of FIG. 3A in accordance with some embodiments.

Referring to FIG. 3B, a top perspective of the first coin 300 of FIG. 3A is illustrated in accordance with some embodiments. Referring to FIG. 3C, a bottom perspective of the first coin 300 of FIG. 3A is illustrated in accordance with some embodiments. As is shown in FIGS. 3A-3C, in one embodiment, the coin 300 may have a closed curved shape (such as a circle or an ellipse). The coin 300 may have a first side 302 that is parallel to a second side 304, wherein each of the first and second sides 302-304 are substantially flat. The coin 300 may be described as being formed in a disc shape including a curved perimeter, a top surface and a bottom surface oriented in parallel with the top surface. The embodiment in which the coin 300 has a closed curved shape with two opposing, parallel sides that are each substantially flat is advantageous at least because such a shape provides a stable surface for the coin 300 to rest on the heating apparatus described below. However, the coin 300 is now limited to a closed curved shape with two opposing, parallel sides that are each substantially flat.

In some embodiments, the coins disclosed herein may be formed from 1.0-3.0 grams of plant material, e.g., lavender, sage, makko powder, Palo Santo, etc., or any combination thereof. In some embodiments, the coins disclosed herein may be formed from 1.8-2.2 grams of plant material. Additionally, the coins formed from 1.8-2.2 grams of plant material and the application of pressure within a range of 1800 to 4000 PSI, e.g., approximately 3800 PSI. Specifically, the coins formed from 1.8-2.2 grams of plant material may be held together due to the combination of the application of pressure and the natural moisture content of the plant material(s) naturally binding the loose plant product together.

Other embodiments may include: (1) sage (loose leaf) by weight percent of 75%, and lavender (loose leaf) by weight percent of 25%; (2) sage (loose leaf) by weight percent of 70%, and lavender (loose leaf) by weight percent of 30%; (3) sage (loose leaf) by weight percent of 99.75%, and makko powder by weight percent of 0.25%; (4) Palo Santo (shredded) by weight percent of 99.75%, and makko powder by weight percent of 0.25%; (5) lavender (loose leaf) by weight percent of 99.75%, and makko powder by weight percent of 0.25%, (6) sage (loose leaf) by weight percent of 79.8%, lavender (loose leaf) by weight percent of 19.95%, and makko powder by weight percent 0.25%; and (7) sage (loose leaf) by weight percent of 79.8%, Palo Santo (shredded) by weight percent of 19.95%, and makko powder by weight percent 0.25%. However, other ratios of various combinations have been contemplated and are within the scope of this disclosure.

The coin 300, and other embodiments of coins disclosed herein overcome significant disadvantages of current aromatherapy and/or air purification products. First, the pressed coin is configured to smolder based on the application of heat (e.g., from a heating element such as a light bulb discussed below) as opposed to the requirement to provide a flame, and often times, continuously application of a flame. Second, various embodiments of the pressed coin may be configured to smolder for a specific and predetermined amount of time, such as 11-15 minutes. The specific and predetermined amount of time may be based on the material(s) used, the amount of each material used, and the amount of pressure applied. In contrast, merely placing raw, unpressed plant product in an open flame or applying heat, such as from a light bulb, the raw, unpressed plant product will ignite and the benefits received from the smoldering (the flavonoids presented in the resulting smoke) will be minimal and disappear within a matter of seconds. This occurs even when the same amount (by weight) of raw, unpressed plant product is placed on the heating element discussed below in comparison to a pressed coin being placed on the heating element discussed below. Therefore, the pressed coin as disclosed herein improves the current state of aromatherapy and/or air purification by overcoming the downfalls of the current products set forth above and discussed herein.

Figure 4A:
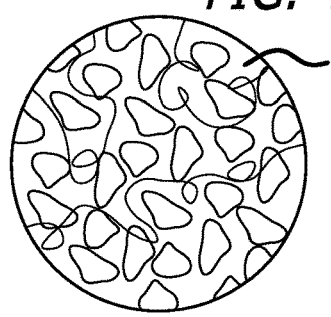
FIG. 4A is an illustration of a top perspective of a second coin in accordance with some embodiments.

Referring to FIG. 4A, a top perspective of a second coin is illustrated in accordance with some embodiments. The coin 400 is sage pressed at a PSI range from 1000 PSI to 36000 PSI. Specifically, the coin 400 may be formed by application of pressure within a range of 1800 to 4000 PSI, e.g., approximately 3800 PSI.

Figure 4B:
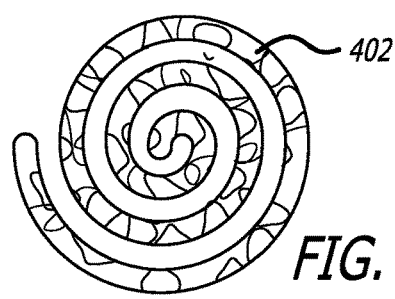
FIG. 4B is an illustration of an alternative embodiment of the second coin in accordance with some embodiments.
Figure 11:
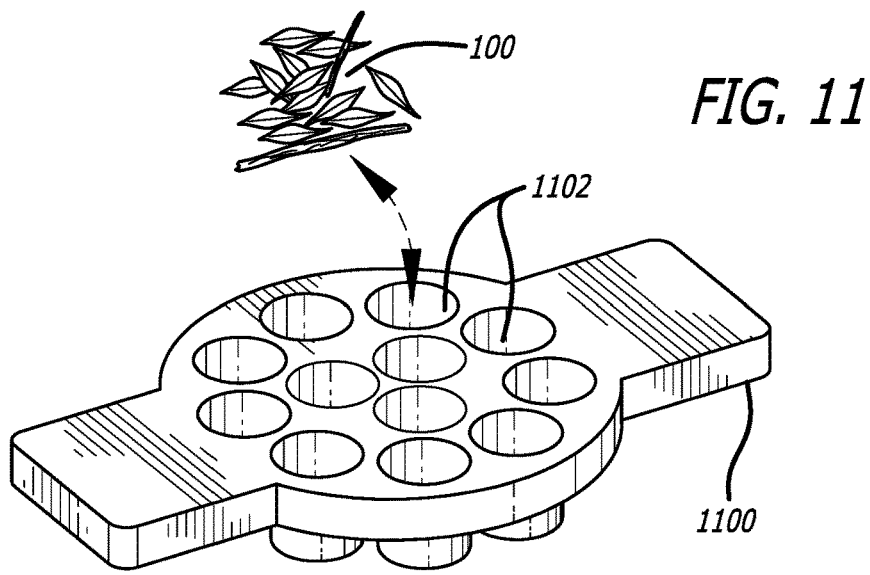
FIG. 11 is an illustration of a top perspective of a bottom press plate in accordance with some embodiments.
Figure 12:
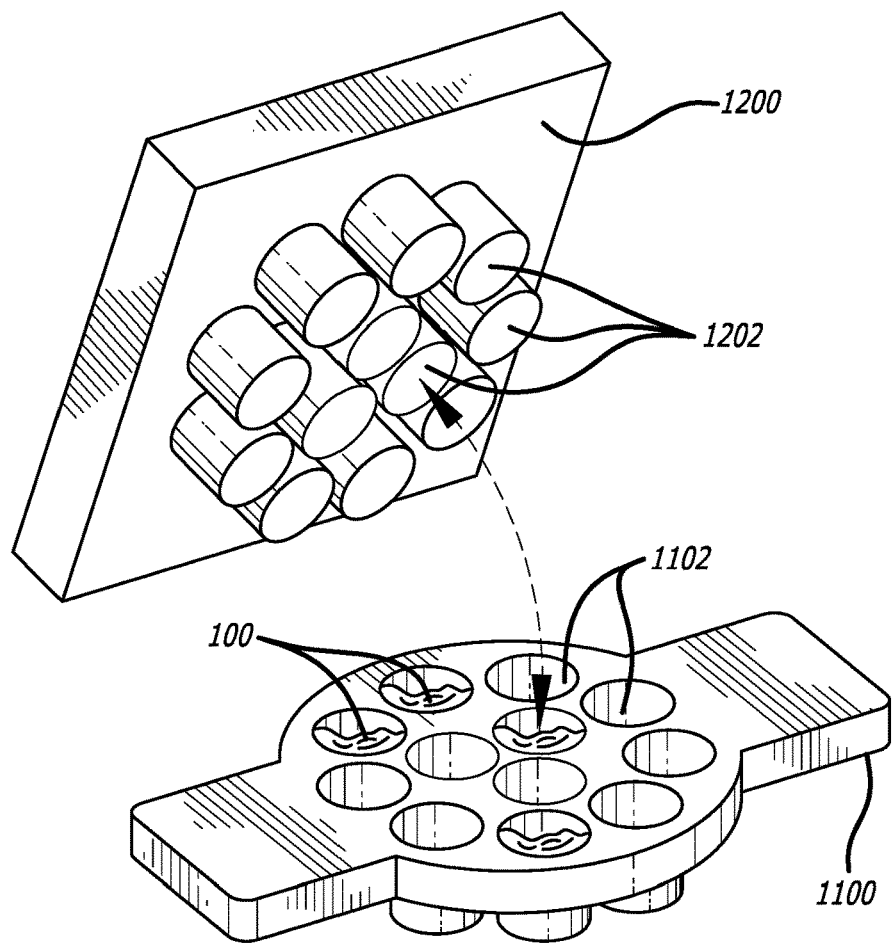
FIG. 12 is an illustration of a top press plate in accordance with some embodiments.

Referring to FIG. 4B, an alternative embodiment of the second coin 400 is shown in accordance with some embodiments. The coin 400 is may be formed from the same material and in the same manner as the coin 400 but may have a spiral shape providing ventilation during the burning process. The spiral shape may be formed based on a design that is machine-cut or laser-cut into the top or bottom press plate as discussed below. For example, the spiral shape may be formed as a raised surface directly in the chambers 1102 or on the cylinders 1202 as seen in FIGS. 11-12.

Figure 5:
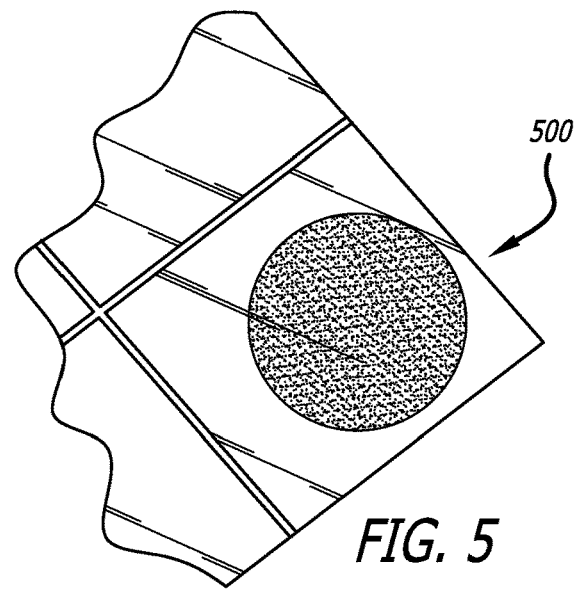
FIG. 5 is an illustration of a top perspective of a third coin individually packaged is illustrated in accordance with some embodiments.

Referring to FIG. 5, a top perspective of a third coin individually packaged is illustrated in accordance with some embodiments. The coin 500 is powdered Palo Santo pressed at a PSI range from 1000 PSI to 36000 PSI. Specifically, the coin 500 may be formed by application of pressure within a range of 15000 to 20000 PSI, e.g., approximately 18000 PSI. In some embodiments, as seen in FIG. 5, coins may be individually packaged for shipment. As shown, the coin 500 is individually packaged in package 502.

Figure 6:
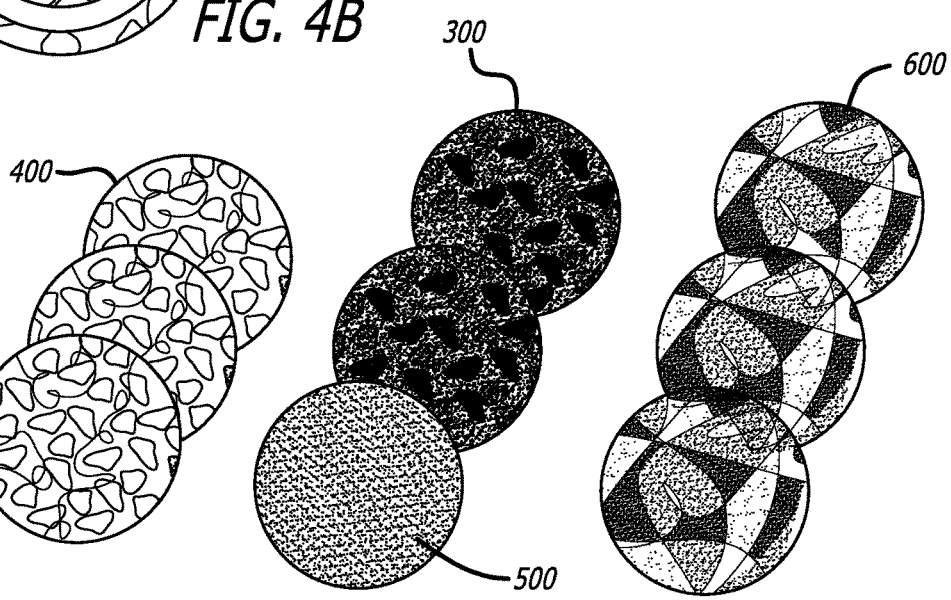
FIG. 6 is an illustration of a top perspective of a plurality of coins is illustrated in accordance with some embodiments.

Referring to FIG. 6, a top perspective of a plurality of coins is illustrated in accordance with some embodiments. Coins 300, coins 400, coin 500 and coins 600 are shown. In particular, coins 600 are comprised of sandalwood that is pressed together at a pressure within a PSI range of 1000-36000 PSI. In one particular embodiment, the coins 600 are each formed are a result of applying pressure within a range of 15000 to 20000 PSI, e.g., approximately 18000 PSI, to the sandalwood. In some embodiments, the coins 600 may comprised sandalwood and makko powder. In one exemplary embodiment, the percentages by weight compared to total weight of each of the coins 600 per formulation are: (1) sandalwood by weight percent of 99.75% and (2) makko powder by weight percent 0.25%.

It should be noted that the coins disclosed herein may be formed from a combination with other materials such as (i) plants, (ii) spices, (iii) essential oils and/or flavonoids. Such materials may include, but are not limited or restricted to, herbs, flowers, wood, lavender, peppermint, lemon, eucalyptus, frankincense resin, tea tree, chamomile, rosemary, jasmine, cedar wood, myrrh, lemongrass, pine, sage, desert sage, clove, cinnamon, dandelion, chamomile, ginger, basil, white sage, rosemary, thyme, lilac, rose, amaranth, Ylang-ylang, mugwort, aspen, blue spruce, sweet grass, Palo Santo, and juniper. In some embodiments, the flowers or herbs may include *Cannabis* and specifically any species thereof such as *Cannabis sativa* (including *C. ruderalis*), *Cannabis indicia*, and/or *Cannabis ruderalis*. The material used may be in any form such as loose leaves, powder, shavings, petals, essential oil, etc. In one example, a coin is formed from a combination of loose leaf sage, Palo Santo and frankincense resin. In various embodiments discussed herein, the frankincense resin may have the form of crystals (or "tears," which is a term often used in the art). With respect to the inclusion of *Cannabis*, in addition to use of the unprocessed, raw plant material, a powdered form may be included as well as *Cannabis* oils in any combination of materials used to create a coin as discussed herein. More specifically, the cannabinoids utilized in creating coins may refer to one or more of THC (tetrahydrocannabinol) and CBD (cannabidiol). However, any cannabinoid acid may be included such as CBGA (Cannabigerolic acid), THCA (49-tetrahydrocannabinolic acid), CBDA (Cannabidiolic acid), CBCA (Cannabichromenenic acid), CBGVA (Cannabigerovarinic acid), THCVA (Tetrahydrocanabivarinic acid), CBDVA (Cannabidivarinic acid) and/or CBCVA (Cannabichromevarinic acid).

Further, it should also be noted that the disclosed invention provides an advantage over current products due to the efficiency in forming the coins. For example, in order to generate a single pound of lavender essential oil, 250 pounds of plant product are required. However, 100% or nearly 100% of the unprocessed, raw plant product placed in the coin press plate apparatus, discussed below, is used when form a coin. Therefore, the coins disclosed herein provide a significant advancement in efficiency of unprocessed, raw product utilized in formation as opposed to current aromatherapy and/or air purifying products. Other essential oils provide additional context in illustrating the advantage provided by the disclosed invention. To form a single pound of essential oil, the following quantities of plant products are required: 10,000 pounds of rose petals, 6,000 pounds of melissa plant (lemon balm), and 1,500 lemons.

II. Heating Apparatus

Figure 7A:
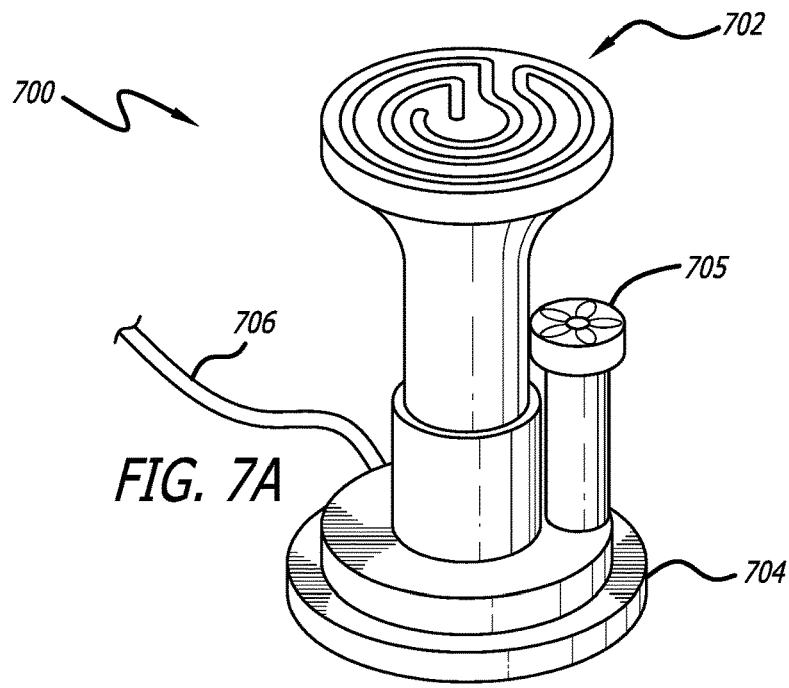
FIG. 7A is an illustration of a heating apparatus is illustrated in accordance with some embodiments.

Referring to FIG. 7A, a heating apparatus is illustrated in accordance with some embodiments. The heating apparatus 700 includes heating element 702, which may be, for example, a ceramic bulb. In some embodiments, a ceramic bulb has a wattage range of 60-150 w, and may provide up to 10,000 hours of light/heat. In one specific embodiment, the heating element 207 may be an E27 ceramic bulb ranging wattage from 50 w-150 w; however, other bulbs having varying wattages have been contemplated and are within the scope of the disclosure. The heating element 702 provides the constant heated surface on which the coins 300-600 are ignited. The heating element 702 is coupled to a base 704 via a socket (e.g., socket 802 of FIG. 8, which may be an E27 socket). The heating element 702 is supplied electricity from power source 706. The heating element 702 may include an upper surface 701 configured to apply heat directly or indirectly to a coin such as the coin 400. In some embodiments, the heating element 702 includes a flat top surface. Other embodiments may include ridges on a top surface (e.g., as shown in FIG. 7A). In some embodiments this surface is concave for collecting ash. The heating element 702 may also include a body component configured to provide spacing between the upper surface 701 and the base 704 as seen in FIG. 7A. The body component may include coupling components, e.g., on a bottom surface, that operably couple the heating element 702 with the base 704 via second coupling components located on the base 704. An optional fan component 705 may be located on the base 704 and facilitate distribution of smoke and/or other aromatics into the surrounding environment during the burning process.

The heating apparatus is connected to a power source 706, which may be rated at 120V or 220V. The power source 706 supplies power to power through the socket 802, which enables the heating element 702, and optionally the fan 705, to operate. The embodiment is supported by base element 704, which supports the heating element and the socket 802, and houses a power unit (not shown) that couples to the power source 706.

In some embodiments, the heating element 702 may be a networked device, e.g., an Internet of Things (IoT) device, often referred to as a "smart device." The smart device, or smart bulb, may couple with a second network device via a network and enable a user to control operation of the smart bulb via the second network device (e.g., a mobile device, tablet, or smart hub such as a Google HOME™, Google HOME HUB™, Amazon ECHO®, etc. Control of the smart bulb may include intensity (e.g., affecting the heat applied to a coin), the color of displayed by the smart bulb, and duration the smart bulb is lit.

Figure 7B:
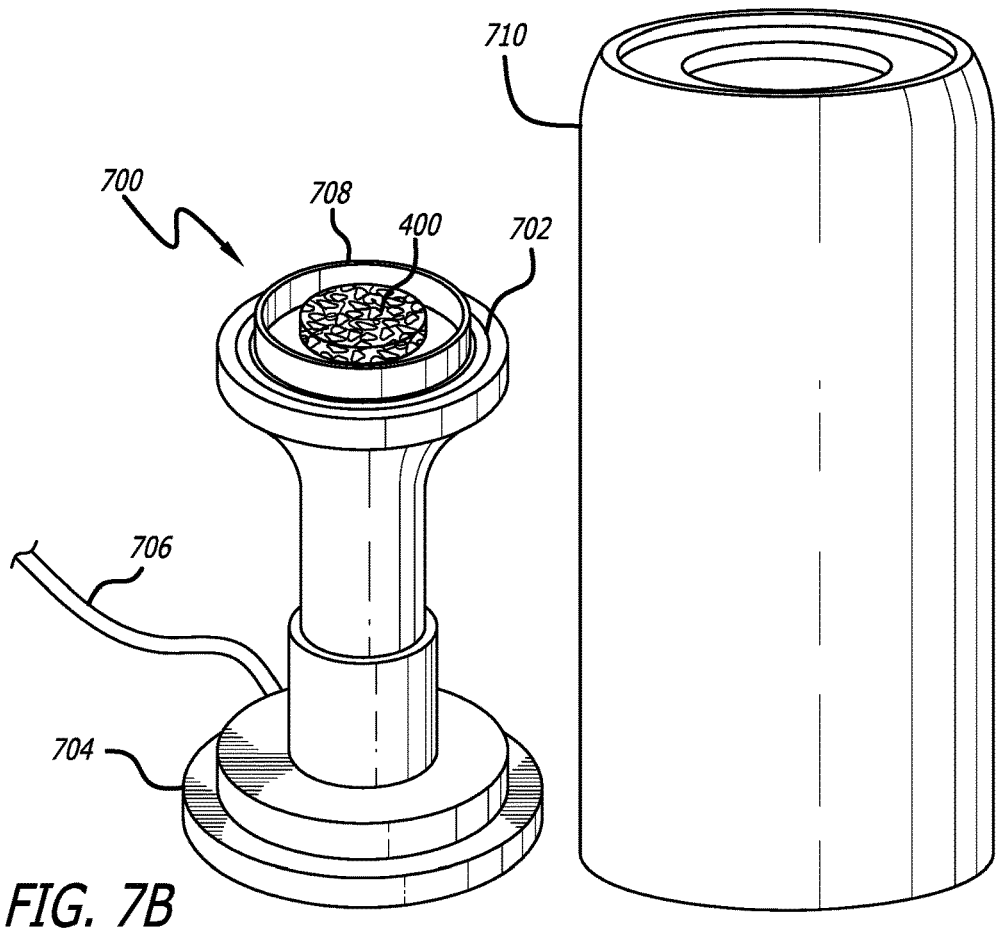
FIG. 7B is an illustration of the heating apparatus 700 of FIG. 7A in accordance with some embodiments.

Referring to FIG. 7B, the heating apparatus 700 of FIG. 7A is illustrated in accordance with some embodiments. The heating apparatus 700 is shown as including an optional heating plate 708, such as a copper bowl, that collects the ashes of a burnt or smoldered coin. The copper plate sits above the heating element 702 with the coin 400 placed therein. The optional heating plate 708 may be securely removable to the heating element 702 thereby providing a secure location where then any coin, in particular, coin 400 may be heated. For example, the plate 708 may removably couple to the heating element 702 may a threaded coupling on the bottom of the heating plate 708 and the top of the heating element 702.

In some embodiments, the base 704, may contain LEDs 904A-904C. The LEDs are for cosmetic aesthetics and are powered by power unit 706. In some embodiments, the base 704 may contain a concave ring, where essential oils or liquids may be poured, with the heat from the heating element 702 causing evaporation thereof.

In other embodiments, although not shown, the base 704 may include an audio device, such as a speaker. For example, the speaker my form a lower portion of the base 704 wherein the speaker is separated from the heating element 702. In some embodiments, the base 704 also includes an integrated circuit (IC) that is configured with logic to: (i) receive wired or wireless communications from a network device, such as a mobile phone, via a network communications interface also integrated into the base 704; and/or (ii) access memory that has stored thereon audio files, such as guided mediation, music or the like. The IC may be configured to cause the audio to be played through the speaker. The wired or wireless communication may be through various communication protocols, e.g., the BLUETOOTH® communications protocol. Further, the wired or wireless communication received by the IC via the network communications interface may control the audio playback (start, stop, pause, change audio file, volume, etc.).

The term "communication" generally refers to related data that is received, transmitted, or exchanged within a communication session. The data may include a plurality of packets, where a "packet" broadly refers to a series of bits or bytes having a prescribed format. Alternatively, the data may include a collection of data that may take the form of an individual or a number of packets carrying related payloads, e.g., an audio file received over a network. Further, the term "logic" may be representative of hardware, firmware or software that is configured to perform one or more functions. As hardware, the term logic (or component) may include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semi-conductor memory, or combinatorial elements.

Additionally, or in the alternative, the logic (or component) may include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic (or component) may be stored in persistent storage.

Figure 10A:
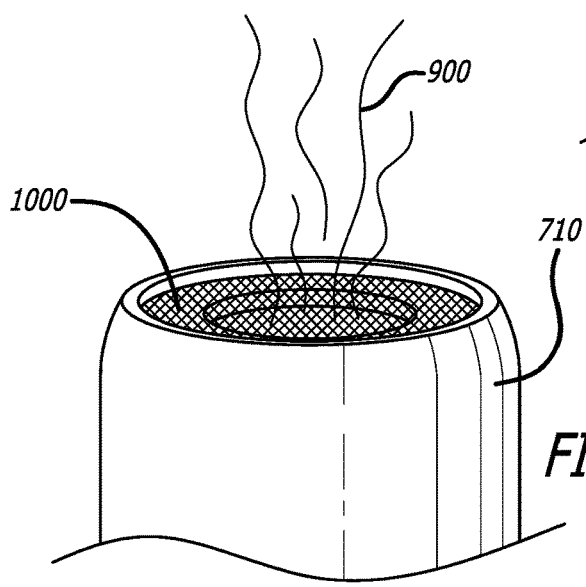
FIG. 10A is an illustration of the optional cover 710 of FIGS. 7A-7B including a filter covering coupled thereto in accordance with some embodiments.

Further, an optional cover 710, a ceramic cover that protects the embodiments, is shown, which may be placed over the heating element 702. In some embodiments, the cover 710 couples to the base element 704 (e.g., via a threaded coupling). In some embodiments, the cover 710 includes a filter mesh on top, which may take the form of numerous materials including carbon filter mesh (as seen in FIG. 10A). In some embodiments, the cover 710 may include a handle (not shown) that facilitates lifting of the cover 710 to provide ease of access to the heating element 702 and/or the heating plate 708. The handle may be removably coupled to the cover 710 via the exterior of the cover 710. In other embodiments, the handle may be removably coupled to the cover 710 via the interior of the cover 710.

Figure 7C:
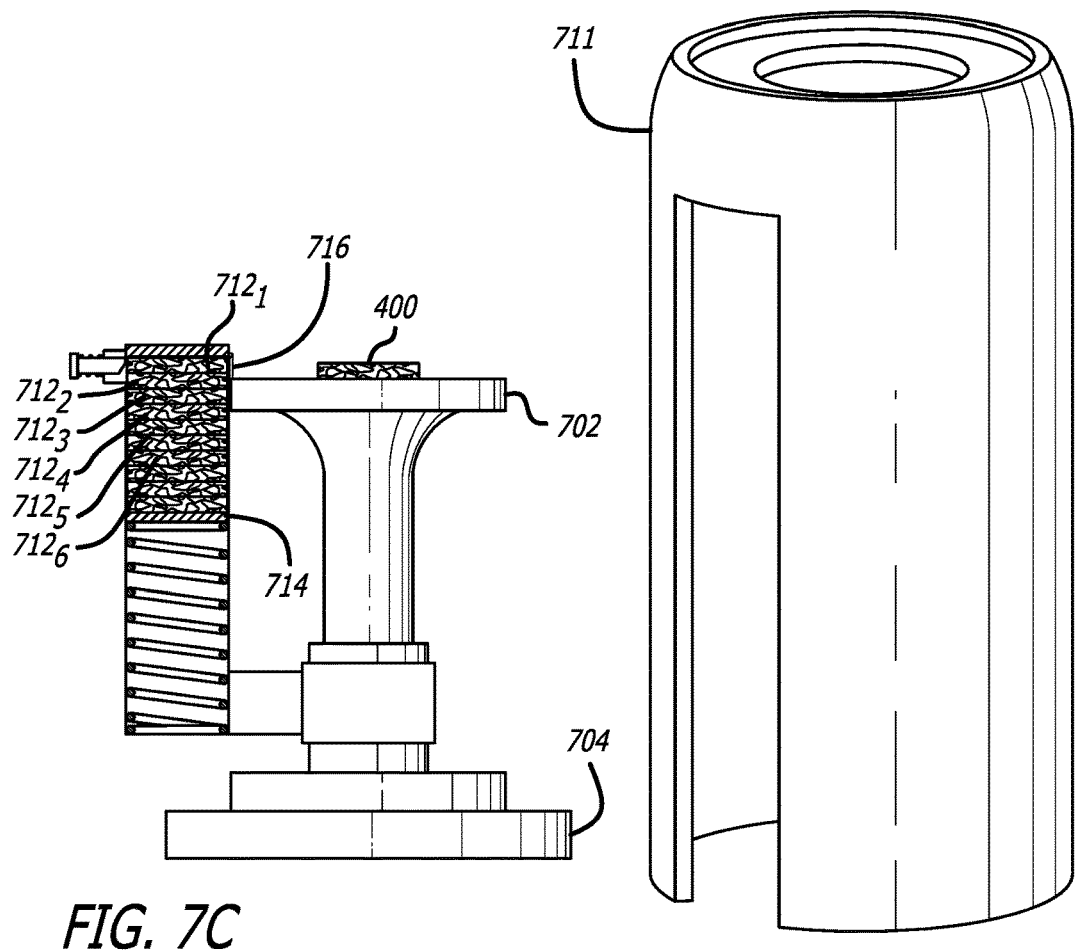
FIG. 7C is an illustration of the heating apparatus of FIGS. 7A-7B including a coin dispensing mechanism in accordance with some embodiments.

Referring now to FIG. 7C, the heating apparatus of FIGS. 7A-7B is shown including a coin dispensing mechanism in accordance with some embodiments. The heating apparatus 700 includes a coin dispensing mechanism 714 having a body that couples with the base 704 and is located adjacent to the heating element 702. The dispensing mechanism 714 is configured to store and dispense coins $712_1$-$712_M$ (wherein M≥1 and M=6 in FIG. 7C). The dispensing mechanism 714 includes a door or gate 716 that may be opened as a result of a user pressing a button (not shown) on the dispensing mechanism 714 and/or may be electronic such that the opening of the door or gate 716 may be controlled via a network communication received from a network device, for example a mobile phone or smart watch, over a wired or wireless network. The dispensing mechanism 714 may include a spring loaded plunger that pushes the coins $712_1$-$712_M$ up when the door or gate 716 is opened. The body of the dispensing mechanism 714 may be insulated so at to protect the coins $712_1$-$712_M$ from the heat generated by the heating element 702. Additionally, the coins $712_1$-$712_M$ may be loaded from the top or bottom of the body of the dispensing mechanism 714 (e.g., a screw cap may be removable coupled). As an alternative, the coins $712_1$-$712_M$ may be loaded via a door on the side of the body of the dispensing mechanism 714 that swings open and closed. In some embodiments, a plurality of dispensing mechanisms 714 may be coupled to the base 704. Additionally, FIG. 7C illustrates the cover 711, which represents an alternative embodiment of the optional cover 710. The cover 711 includes a slit or cut-out for placement over a heating apparatus that includes a dispensing mechanism 714.

Figure 7D:
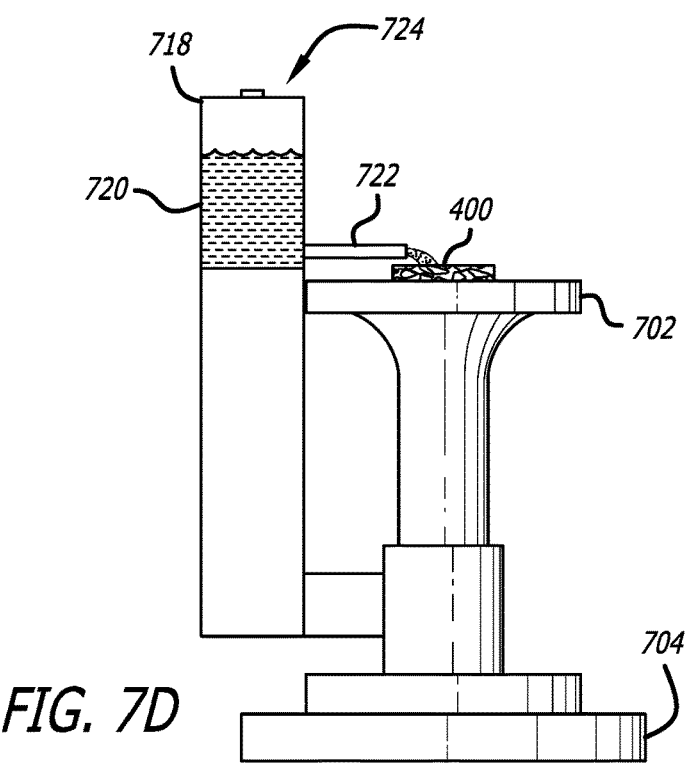
FIG. 7D is an illustration of the heating apparatus of FIGS. 7A-7B including a liquid dispensing mechanism in accordance with some embodiments.

Referring now to FIG. 7D, the heating apparatus of FIGS. 7A-7B is shown including a liquid dispensing mechanism in accordance with some embodiments. The heating apparatus 700 includes a liquid dispensing mechanism 718 having a body that couples with the base 704 and is located adjacent to the heating element 702. The liquid dispensing mechanism 718 is configured to store and dispense liquid 720, e.g., an essential oil. The liquid 720 may be loaded via the top of the liquid dispensing mechanism 718 by unscrewing a cap 724. The liquid 720 may be dispensing via a nozzle 722. The nozzle 722 may be activated (e.g., allow liquid to pass) as a result of a user pressing a button, for example located on the top of the dispensing mechanism 714. In some embodiments, the nozzle 722 may be activated electronically and may be controlled via a network communication received from a network device, for example a mobile phone or smart watch, over a wired or wireless network. In some embodiments, a plurality of liquid dispensing mechanisms may be coupled to the base 704. Further, in some embodiments, one or more liquid dispensing mechanisms 718 and one or more dispensing mechanisms 714 may be coupled to the base 704.

Figure 8:
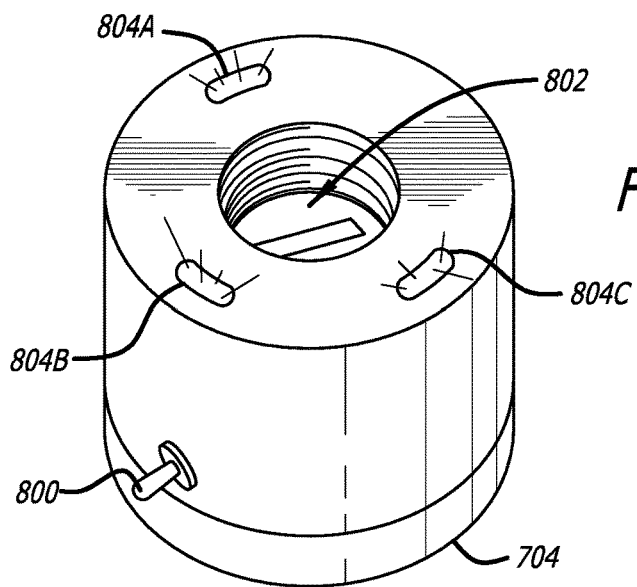
FIG. 8 is an illustration of the base element 704 of FIGS. 7A-7B in accordance with some embodiments.

Referring to FIG. 8, the base element 704 of FIGS. 7A-7B is illustrated in accordance with some embodiments. The base element 704 is illustrated in as an alternative embodiment to that illustrated in FIGS. 7A-7D and includes a power switch 800, an aperture 802 and one or more optional light emitting diodes 804A-804C on some embodiments. The light emitting diodes 804A-804C are powered from the power source 706 (as seen in FIGS. 7A-7B).

Figure 9:
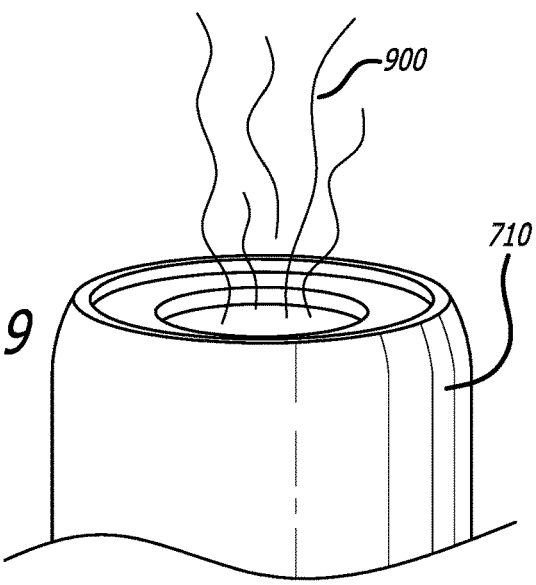
FIG. 9 is an illustration of the optional cover 710 of FIGS. 7A-7B is illustrated in accordance with some embodiments.

Referring to FIG. 9, the optional cover 710 of FIGS. 7A-7B is illustrated in accordance with some embodiments. The ignition or combustion of coins 300-600 results in smoke 900 that emanates from an opening in the cover 710. The combustion is a result of the heating element 702 surface heating directly or indirectly contacting the coins 300-600.

Referring to FIG. 10A, the optional cover 710 of FIGS. 7A-7B is illustrated as having a filter covering 1000 coupled thereto in accordance with some embodiments. The filter covering 1000 may be formed from various materials and may take the form of a mesh screen. In some embodiments, the filter covering 1000 may be formed from one or more of metal, fiberglass or other fiber-reinforced plastic using glass fiber, plastic, carbon and/or paper. The filter covering 1000 may remove some aspects of the smoke 900 as the smoke 900 passes through the filter covering 1000 providing a slightly purified emission from the heating apparatus 700.

Figure 10B:
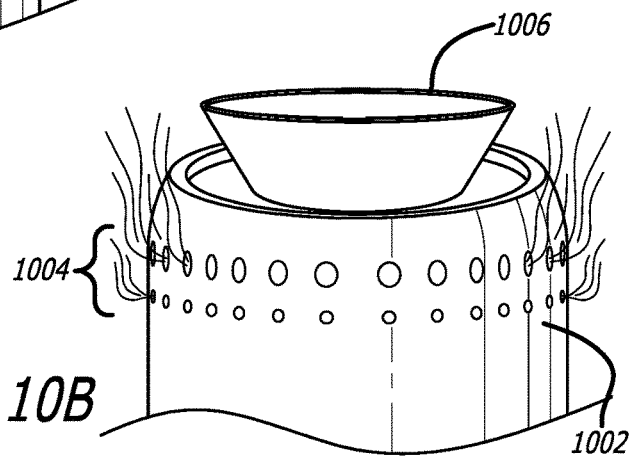
FIG. 10B is an illustration of an alternative embodiment of an optional cover including a dish coupled thereto in accordance with some embodiments.

Referring to FIG. 10B, an alternative embodiment of the optional cover 711 is illustrated as having a dish coupled thereto in accordance with some embodiments. The cover 1002 includes and a plurality of ventilation holes 1004 that allow the smoke 900 to emanate therefrom. The top of the cover 1002 also includes a dish 1006 located thereon. The dish 1006 may be formed from various materials and may be specifically sized and configured for placement on a top of a cover, such as the cover 1002, which may have a similar opening as seen on the cover 710. The dish 1006 may rest on top of the cover 1002 with a bottom portion of the dish 1006 exposed to the interior of the cover. In some embodiments, the dish 1006 may be formed from one or more of metal, ceramic, glass, fiberglass or other fiber-reinforced plastic using glass fiber and/or carbon. The dish 1006 may retain additional materials and/or liquids to which the heat from the heating element 702 may be applied. The additional materials and/or liquids may include, but are not limited or restricted to, additional coins, water, incense, essential oils, perfumes, etc.

Coin Press Apparatus

Referring to FIG. 11, a top perspective of a bottom press plate 1100 is illustrated in accordance with some embodiments. The bottom press plate 1100 includes a plurality of chambers 1102 where a biomass such as unprocessed, raw plant stock (and optionally combinations of various materials, fragrances and/or essential oils) is loaded by various methods into the chambers 1102, and pressure is applied from the top plate press 1200 of FIG. 12. As illustrated, biomass 100 is seen being loaded into the chambers 1102.

Referring to FIG. 12, the top press plate 1200 is illustrated in accordance with some embodiments. The top press plate 1200 includes a plurality of cylinders 1202 that correspond to and align with the plurality of chambers 1102 of the bottom press plate. The chambers 1102 are configured to receive the cylinders 1202 such that pressure applied to the top of the top press plate compresses the biomass located within the chambers 1102. As referred to herein, the top of the top press plate may be the side opposite the cylinders 1202. The top press plate and bottom press plate comprise a press plate apparatus.

Figure 13:
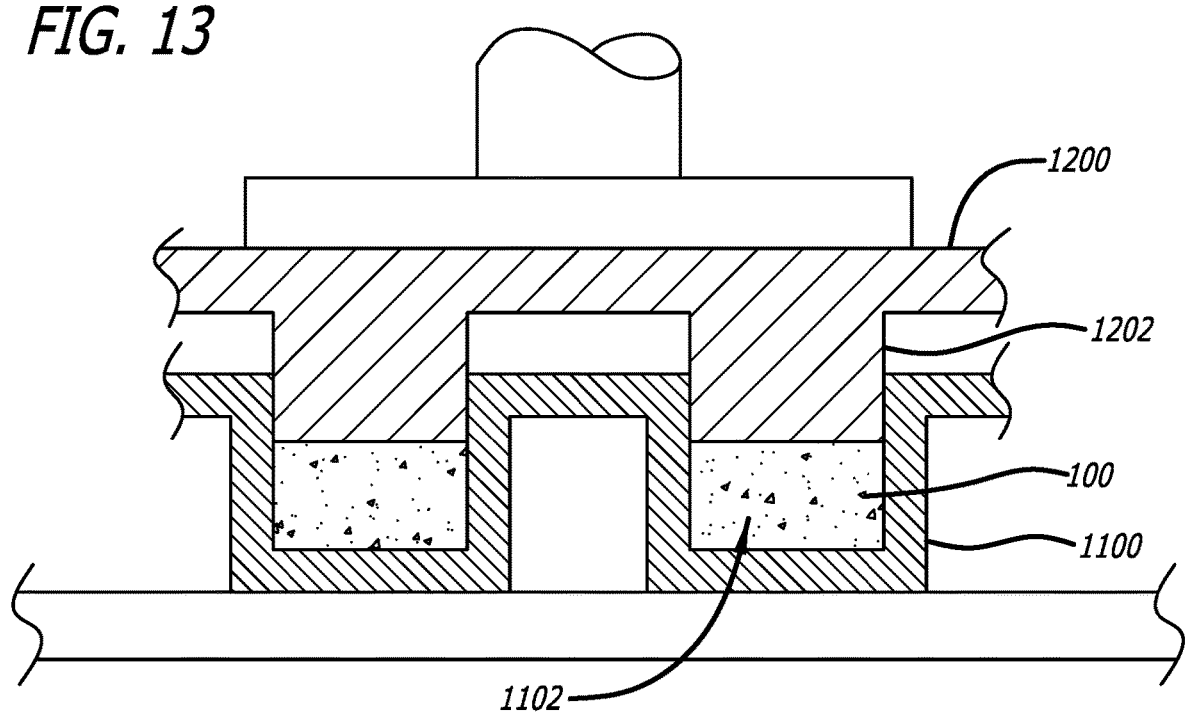
FIG. 13 is an illustration of a biomass placed within the chambers of the bottom press plate in accordance with some embodiments.
Figure 14:
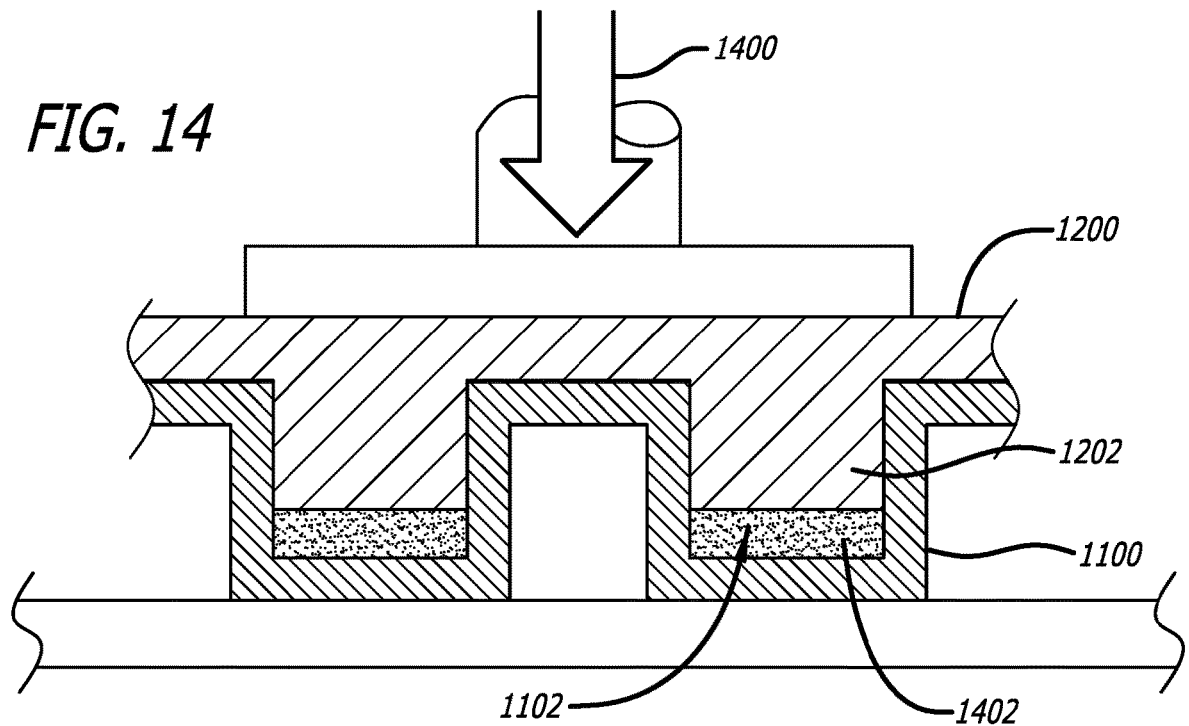
FIG. 14 is an illustration of a plurality of cylinders of the top press plate of FIG. 12 in a second, compressed position in accordance with some embodiments.

Referring now to FIG. 13, biomass 100 is shown within the chambers 1102 of the bottom press plate 1100. The cylinders 1202 of the top press plate 1200 are shown in an initial position aligned with and partially inserted into the chambers 1102. Referring now to FIG. 14, the cylinders 1202 of the top press plate 1200 are shown in a second, compressed position. Based on the application of the pressure 1400 to the top press plate 1200, the resultant pressed biomass component 1402 (i.e., a coin) has been formed.

In the foregoing description, the invention is described with reference to specific exemplary embodiments thereof. It will, however, be evident that various modifications and changes may be made thereto without departing from the broader spirit and scope of the invention as set forth in the appended claims.

What is claimed is:

1. A pressed biomass component comprising:
   plant material comprising loose leaf sage, wherein the plant material is compressed by a press plate apparatus by application of pressure within a range of 25000 to 36000 pounds per square inch (PSI), wherein the pressed biomass component is a resultant of the application of the pressure to the plant material, and the pressed biomass component has a weight of 0.5-10 grams,
   wherein the pressed biomass component is bound together by natural moisture content of the plant material that is extracted during compression of the plant material, and wherein binding of the pressed biomass component is without use of additional binding agents.

2. The pressed biomass component of claim 1, wherein pressed biomass component formed in a disc shape including a curved perimeter, a top surface and a bottom surface oriented in parallel with the top surface.

3. The pressed biomass component of claim 2, wherein the application of pressure forms the pressed biomass component to support a desired burn time when placed on a heating apparatus, and wherein the heating apparatus includes a ceramic bulb having a wattage within a wattage range of 50 w-150 w.

4. The pressed biomass component of claim 1, wherein the desired burn time is within a range of 11-15 minutes.

5. The pressed biomass component of claim 1, wherein the range of pressured applied is 30000-36000 PSI.

6. The pressed biomass component of claim 1, wherein the plant material comprises loose leaf white sage.

7. The pressed biomass component of claim 1, wherein the plant material comprises the loose leaf sage by a weight percentage ranging from seventy to seventy-seven percent (70-77%) of a total weight of the pressed biomass component.

8. The pressed biomass component of claim 7, wherein the plant material further comprises lavender by a weight percentage ranging from twenty to twenty-seven percent of a total weight of the pressed biomass component.

9. The pressed biomass component of claim 8, wherein the plant material further comprises makko powder by a weight percentage ranging from 0.1 to 2-percent of a total weight of the pressed biomass component.

10. A method for producing a pressed biomass component, the method comprising:
    placing plant material in a bottom press plate of a press plate apparatus, wherein the plant material comprises loose leaf sage or shredded Palo Santo;
    aligning a top plate of the press plate apparatus with the bottom press plate;
    applying pressure to one or more of the top press plate or the bottom press plate, wherein the pressure is within a range of 2500 to 36000 pounds per square inch (PSI), wherein the pressed biomass component is a resultant of the application of the pressure to the plant material, and the pressed biomass component has a weight of 0.5-10 grams;
    separating the top press plate and the bottom press plate; and
    removing the pressed biomass component from the bottom press plate, wherein the pressed biomass component is bound together by natural moisture content of the plant material that is extracted during compression of the plant material, and wherein binding of the pressed biomass component is without use of additional binding agents.

11. The method of claim 10, wherein the bottom press plate includes a plurality of chambers for receiving the plat material, and the top press plate includes a plurality of cylinders corresponding to the plurality of chambers of the bottom press plate.

12. The method of claim 10, wherein pressed biomass component is formed in a disc shape including a curved perimeter, a top surface and a bottom surface oriented in parallel with the top surface.

13. The method of claim 10, wherein the application of pressure forms the pressed biomass component to support a desired burn time when placed on a heating apparatus, wherein the heating apparatus includes a ceramic bulb having a wattage within a wattage range of 50 w-150 w.

14. The method of claim 13, wherein the desired burn time is within a range of 11-15 minutes.

15. The method of claim 12, wherein the range of pressured applied is 30000-36000 PSI.

16. The method of claim 10, wherein the plant material comprises loose leaf white sage.

17. The method of claim 10, wherein the plant material comprises the loose leaf sage by a weight percentage ranging from seventy to seventy-seven percent (70-77%) of a total weight of the pressed biomass component.

18. The method of claim 10, wherein the plant material further comprises lavender by a weight percentage ranging from twenty to twenty-seven percent of a total weight of the pressed biomass component and makko powder by weight eight percentage ranging from 0.1 to 2-percent of a total weight of the pressed biomass component.

19. The method of claim 10, wherein the plant is shredded Palo Santo.

20. The pressed biomass component of claim 1, wherein the pressed biomass component is formed from 1.0-2.2 grams of the plant material.

21. A pressed biomass component comprising:
plant material comprising shredded Palo Santo, wherein the plant material is compressed by a press plate apparatus by application of pressure within a range of 25000 to 36000 pounds per square inch (PSI), wherein the pressed biomass component is a resultant of the application of the pressure to the plant material, and the pressed biomass component has a weight of 0.5-10 grams,
wherein the pressed biomass component is bound together by natural moisture content of the plant material that is extracted during compression of the plant material, and wherein binding of the pressed biomass component is without use of additional binding agents.

22. The pressed biomass component of claim 21, wherein the plant material includes 70 percent shredded Palo Santo and 30 percent loose leaf lavender.

23. The pressed biomass component of claim 21, wherein the pressed biomass component is formed from 1.0-2.2 grams of the plant material.

24. The pressed biomass component of claim 21, wherein the application of pressure is within a range of 30000 to 36000 PSI.

* * * * *